(12) United States Patent
Schierle et al.

(10) Patent No.: US 6,896,895 B2
(45) Date of Patent: May 24, 2005

(54) CAROTENOID ESTERS, CAROTENOID-ENRICHED FEEDS, AND METHODS OF PIGMENTING FOODS AND FOODSTUFFS

(75) Inventors: Joseph Schierle, Bad Krozingen (DE); Werner Simon, Riehen (CH); Wolfgang Steinberg, Loerrach (DE)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 09/950,464

(22) Filed: Sep. 10, 2001

(65) Prior Publication Data

US 2002/0114867 A1 Aug. 22, 2002

(30) Foreign Application Priority Data

Sep. 11, 2000 (EP) ............................................. 00119760

(51) Int. Cl.$^7$ ........................ A61K 47/00; A23K 1/165; A23K 1/17
(52) U.S. Cl. ........................................ 424/439; 424/442
(58) Field of Search ................................. 424/439, 442, 424/489, 400; 514/725

(56) References Cited

U.S. PATENT DOCUMENTS

| | | | |
|---|---|---|---|
| 5,763,651 A | | 6/1998 | Rüttimann .................. 424/402 |
| 5,849,345 A | * | 12/1998 | Giger et al. ..................... 426/2 |

FOREIGN PATENT DOCUMENTS

| | | |
|---|---|---|
| DE | 41 00 739 A1 | 7/1992 |
| EP | 0 630 578 A3 | 12/1994 |
| EP | 0 718 284 A2 | 6/1996 |
| EP | 0 814 078 A1 | 12/1997 |
| FR | 2 187 291 | 1/1974 |

OTHER PUBLICATIONS

Balnave and Bird, "Relative Efficiencies of Yellow Carotenoids For Egg Yolk Pigmentation," *AJAS*, vol. 9, No. 5, pp. 515–517 (1996).

Nys, "Dietary Carotenoids and Egg Yolk Coloration–a Review," *Arch. Geflügelk.*, vol. 64, No. 2, pp. 45–54 (2000).

Baiao, et al., "Pigmenting Efficacy of Several Oxycarotenoids on Egg Yolk," *J. Appl. Poultry Res.*, vol. 8, pp. 472–479 (1999).

Steinberg, et al., "Comparative pigmentation efficiency of two products containing either apo–ester or tagetes extracts in egg yolks and liquid eggs," *Arch. Geflügelk.*, vol. 64, No. 4, pp. 180–187 (2000).

* cited by examiner

*Primary Examiner*—Thurman K. Page
*Assistant Examiner*—Sharon Howard
(74) *Attorney, Agent, or Firm*—Bryan Cave LLP

(57) ABSTRACT

The present invention is a method for pigmenting a food or foodstuff comprising combining in a source of feed, a carotenoid ester of formula I:

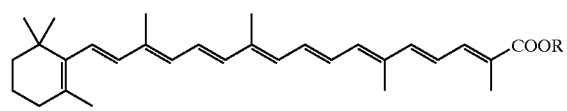

wherein R is methyl, $C_{3-16}$-alkyl, $C_{3-16}$-alkenyl, or $C_{5-8}$-cycloalkyl. Further embraced by the invention are the carotenoid-enriched feeds, e.g., for poultry, fish, or crustacea, premixes for incorporation in such feeds, and beadlets containing the carotenoid ester for incorporation in such premixes. A further aspect of the present invention is carotenoid esters of formula I.

18 Claims, No Drawings

CAROTENOID ESTERS, CAROTENOID-ENRICHED FEEDS, AND METHODS OF PIGMENTING FOODS AND FOODSTUFFS

FIELD OF THE INVENTION

The invention relates to carotenoid esters that are useful for pigmentation in the food and feedstuff industries. The present invention also relates to carotenoid-enriched feeds, e.g., for poultry, fish, or crustacea, premixes for incorporation in such feeds, and beadlets containing the carotenoid esters for incorporation in such premixes. A further aspect of the present invention is carotenoid esters of formula I.

BACKGROUND OF THE INVENTION

It is well known that carotenoids are natural pigments that occur abundantly in the plant and animal kingdoms and which, in some cases, have also been produced by synthetic means. Other carotenoids can be synthetically produced and do not appear to occur in nature. Many important carotenoids are employed as pigments in the food and feedstuff industries, e.g., for coloring egg yolk, poultry, fish, and crustacea, notably in the cases of ethyl beta-apo-8'-carotenoate (CAROPHYLL® Yellow), astaxanthin (CAROPHYLL® Pink), and canthaxanthin (CAROPHYLL® Red). For this purpose the carotenoid pigments are added to the animals' rations as a method of imparting an enhanced and aesthetically more acceptable visual impression of color, be it in the animal integuments, such as the skin, shanks, and beaks of poultry and the skin, scales, and shells of fish and crustacea, as appropriate, subcutaneous fat of poultry and the meat of fish and crustacea, or in such animal products as eggs (egg yolk). The enhancement of pigmentation depends on the particular light-absorbing conjugated double bond system of the carotenoid concerned, the degree of ease with which the carotenoid is taken up into the animal body following consumption of the carotenoid-enriched feed ("deposition rate"), and the concentration of the carotenoid or any metabolites in the target animal body tissue or product, among other factors. However, one cannot predict from the structure of the selected carotenoid how effectively it functions as a pigment in this area of application. A further factor is the stability of the carotenoid, e.g., towards atmospheric oxidation, light, temperature, and dampness, in an animal feedstuff under normal storage conditions.

In poultry an acceptable level and quality of pigmentation is desired for the integuments of the birds destined for consumption, e.g., broilers, and for the egg yolks of laying poultry, e.g., laying hens. Materials are used to enhance yolk color, for example, because consumers prefer deeply (particularly rich golden yellow) pigmented yolks. The visual appearance of food is an important factor in the assessment of quality. In many parts of the world broilers and ornamental birds, for example, are more aesthetically acceptable if their integuments, particularly skin, shanks, and beaks, and, in the case of broilers, also subcutaneous fat satisfy certain criteria of pigmentation. The need for supplementary pigmentation is especially prevalent today in view of the reduction of grass consumption in the modern methods of intensive poultry rearing. The use of low fiber, high energy feeds makes the production of well-pigmented poultry and egg yolks difficult.

The pigmentation of fish meat and integuments, especially in various species of trout and salmon, and the meat and integuments of crustacea, e.g., crabs, lobsters, and shrimps, is achieved by feeding the fish and crustacea carotenoid-enriched feed preparations, thereby making the edible products more attractive to consumers.

Moreover, alimentary products such as dairy products, e.g., butter and cheese, and such cosmetic products as lipsticks are pigmentable by incorporation of carotenoids at a suitable stage of the pertinent production processes.

SUMMARY OF THE INVENTION

It has now been found that certain carotenoid esters, as specified below, are surprisingly more effective as pigments in the above-indicated applications than the carotenoid esters, especially ethyl beta-apo-8'-carotenoate, previously used for such purposes.

One embodiment of the present invention is a method for pigmenting a food or foodstuff by combining in a source of feed, a carotenoid ester of formula I:

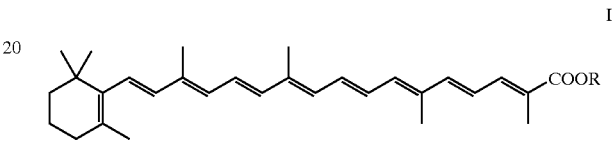

wherein R is methyl, $C_{3-16}$-alkyl, $C_{3-16}$-alkenyl, or $C_{5-8}$-cycloalkyl.

Another embodiment of the present invention is a carotenoid-enriched feed containing a carotenoid ester of formula I:

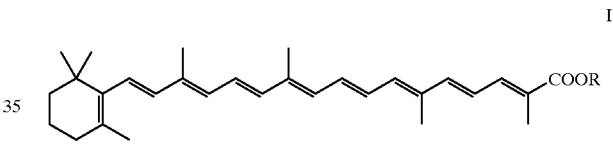

wherein R in methyl, $C_{3-16}$-alkyl, $C_{3-16}$-alkenyl, or $C_{5-8}$-cycloalkyl.

A further embodiment of the present invention is a beadlet containing from about 1 to about 20 percent by weight based on the total weight of the beadlet of a carotenoid ester of formula I:

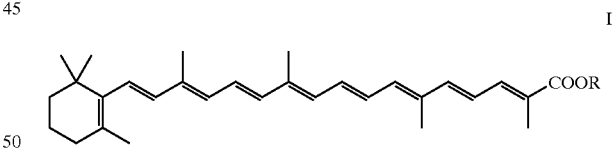

wherein R is methyl, $C_{3-16}$-alkyl, $C_{3-16}$-alkenyl, or $C_{5-8}$-cycloalkyl.

Another embodiment of the present invention is a method for pigmenting an organism by orally administering to the organism an organism-pigmenting quantity of a carotenoid ester of the general formula I:

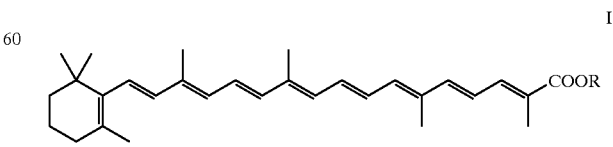

wherein R is methyl, $C_{3-16}$-alkyl, $C_{3-16}$-alkenyl, or $C_{5-8}$-cycloalkyl.

A further embodiment of the present invention is a carotenoid ester selected from the group consisting of n-propyl beta-apo-8'-carotenoate, 2-methyl-butyl beta-apo-8'-carotenoate, 2,2-dimethylpropyl beta-apo-8'-carotenoate, 2-ethyl-1-butyl beta-apo-8'-carotenoate, 2-methyl-1-pentyl beta-apo-8'-carotenoate, 4-methyl-2-pentyl beta-apo-8'-carotenoate, n-lauryl beta-apo-8'-carotenoate, n-cetyl beta-apo-8'-carotenoate, cyclopentyl beta-apo-8'-carotenoate, isopropyl beta-apo-8'-carotenoate, tert. butyl beta-apo-8'-carotenoate, and 2-pentyl beta-apo-8'-carotenoate.

DETAILED DESCRIPTION OF THE INVENTION

One embodiment of the present invention is a method for pigmenting a food or foodstuff by combining in a source of feed, a carotenoid of formula I:

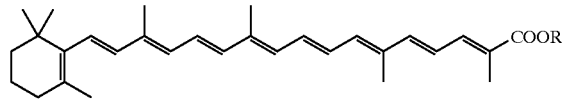

I wherein R is methyl, $C_{3-16}$-alkyl, $C_{3-16}$-alkenyl, or $C_{5-8}$-cycloalkyl.

As used herein, the term "$C_{3-16}$-alkyl" or "$C_{3-16}$-alkenyl" means straight-chain in and branched alkyl and alkenyl groups, respectively, such as, for example, n-propyl, isopropyl, and tert. butyl or, respectively, vinyl and 4-methyl-3-pentenyl. The term "$C_{5-8}$-cycloalkyl" includes, for example, cyclopentyl and cyclohexyl.

Formula I includes isomeric forms of the compounds, e.g., optically active and cis/trans or E/Z isomers, as well as mixtures thereof, unless an isomeric form is specifically indicated. With respect to E/Z isomerism, the all-E isomers are generally preferred.

Preferably, the carotenoid ester of formula I is selected from the group consisting of:

| | | |
|---|---|---|
| methyl beta-apo-8'-carotenoate | CAN: 4273-73-8 | (1) |
| n-propyl beta-apo-8'-carotenoate | | (2) |
| n-butyl beta-apo-8'-carotenoate | CAN: 148216-79-9 | (3) |
| isobutyl beta-apo-8'-carotenoate | CAN: 148216-80-2 | (4) |
| sec. butyl beta-apo-8'-carotenoate | CAN: 148216-81-3 | (5) |
| isoamyl beta-apo-8'-carotenoate | CAN: 148216-83-5 | (6) |
| 2-methyl-butyl beta-apo-8'-carotenoate | | (7) |
| 2,2-dimethylpropyl beta-apo-8'-carotenoate | | (8) |
| 2-ethyl-1-butyl beta-apo-8'-carotenoate | | (9) |
| n-hexyl beta-apo-8'-carotenoate | CAN: 148216-84-6 | (10) |
| 2-methyl-1-pentyl beta-apo-8'-carotenoate | | (11) |
| 4-methyl-2-pentyl beta-apo-8'-carotenoate | | (12) |
| n-lauryl beta-apo-8'-carotenoate | | (13) |
| n-cetyl beta-apo-8'-carotenoate | | (14) |
| cyclopentyl beta-apo-8'-carotenoate | | (15) |
| cyclohexyl beta-apo-8'-carotenoate | CAN: 148216-83-7 | (16) |
| isopropyl beta-apo-8'-carotenoate | | (17) |
| tert. butyl beta-apo-8'-carotenoate | | (18) |
| 2-pentyl beta-apo-8'-carotenoate | | (19) | and mixtures thereof.

Some of the carotenoid esters usable in the method and the carotenoid-enriched feed of the present invention are known per se, and are designated in the above list by their Chemical Abstracts numbers (CAN).

Nothing in the prior art in any way indicates that the known carotenoid esters are useful as pigments in the manner described herein, e.g., for enhancing the color of egg yolk.

More preferably, the carotenoid esters of formula I are selected from those wherein R is $C_{3-16}$-alkyl, especially from the group consisting of the last three listed carotenoid esters, i.e. those numbered (17)–(19).

Another embodiment of the present invention is a carotenoid-enriched feed containing a carotenoid ester of formula I:

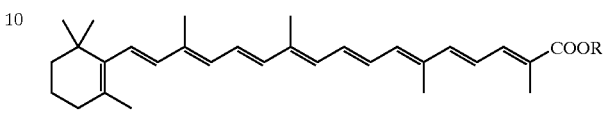

I wherein R is methyl, $C_{3-16}$-alkyl, $C_{3-16}$-alkenyl, or $C_{5-8}$-cycloalkyl.

A further embodiment of the present invention is a beadlet containing from about 1 to about 20 percent by weight based on the total weight of the beadlet of a carotenoid ester of formula I:

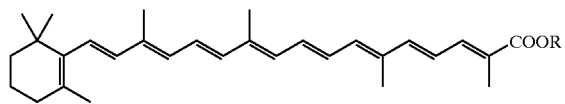

I wherein R is methyl, $C_{3-16}$-alkyl, $C_{3-16}$-alkenyl, or $C_{5-8}$-cycloalkyl.

Another embodiment of the present invention is a method for pigmenting an organism by orally administering to the organism an organism-pigmenting quantity of a carotenoid ester of the general formula I:

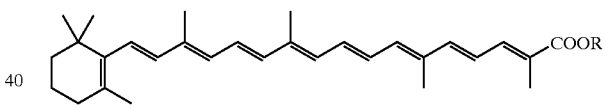

I wherein R is methyl, $C_{3-16}$-alkyl, $C_{3-16}$-alkenyl, or $C_{5-8}$-cycloalkyl.

A further embodiment of the present invention is a carotenoid ester selected from the group consisting of n-propyl beta-apo-8'-carotenoate, 2-methyl-butyl beta-apo-8'-carotenoate, 2,2-dimethylpropyl beta-apo-8'-carotenoate, 2-ethyl-1-butyl beta-apo-8'-carotenoate, 2-methyl-1-pentyl beta-apo-8'-carotenoate, 4-methyl-2-pentyl beta-apo-8'-carotenoate, n-lauryl beta-apo-8'-carotenoate, n-cetyl beta-apo-8'-carotenoate, cyclopentyl beta-apo-8'-carotenoate, isopropyl beta-apo-8'-carotenoate, tert. butyl beta-apo-8'-carotenoate, and 2-pentyl beta-apo-8'-carotenoate.

Preferably, the carotenoid ester in the carotenoid-enriched feed is selected from the above-listed carotenoid esters (1)–(19), more preferably (17)–(19), the carotenoid ester being present in the feed in an effective amount.

The previously unknown carotenoid esters of formula I of the present invention, i.e. those numbered 2, 7–9, 11–15, and 17–19, can be produced from appropriate starting materials by methods analogous to those for producing the known carotenoid esters of similar structure, e.g., ethyl beta-apo-8'-carotenoate (see for example Helv. Chim. Acta 42, 862 ff. (1959), ibid. 49, 369 ff. (1966), Pure Appl. Chem. 14, 245 ff. (1967), Swiss Patent No. 382,148, and Guex, et al., U.S. Pat. No. 3,113,961). Accordingly, the carotenoid esters of formula I can be obtained, for example, a) by transesterification of ethyl beta-apo-8'-carotenoate in the presence of the desired alcohol component and a base (J. March, Advanced Organic Chemistry, $3^{rd}$ Ed; Wiley Interscience, 1985, p. 351); b) by the Wittig reaction of beta-apo-12'-carotenal with (3-alkoxycarbonyl-2-butenyl)-trophenylphosphonium chloride in the presence of a base (Guex, et al., U.S. Pat. No. 3,113,961; Cadogan, Organophosphorus Reagents in Organic Synthesis, Academic Press, New York, 1979); or c) from the mixed anhydride prepared from beta-apo-8'-carotenoic acid and trifluoroacetic acid (R. C. Parish et al., J. Org. Chem. 30, 927 (1965).)

In the method of the present invention, the carotenoid ester is applied to or combined with a feed source for an organism such as, for example, poultry, fish, or crustacea, as appropriate. The carotenoid ester responsible for the enhanced pigmentation is ingested by the pertinent organism in a natural manner. The pertinent feed may also contain other natural and/or artificial (synthetically produced) carotenoids (e.g., as provided in EP 630,578 B1 and EP 718,284 B1) which themselves contribute to the normal pigmentation of, e.g., egg yolk, integuments, and/or subcutaneous fat of poultry and the meat and/or integuments of fish and crustacea. The content the added carotenoid ester of formula I in the feed is from about 0.1 ppm to about 150 ppm (mg/kg or about 0.00001 to about 0.015% by weight) based on the total weight of the carotenoid ester-enriched feed. In poultry feed, particularly for laying hens and broilers, the content of added carotenoid ester(s) is preferably from about 0.25 ppm to about 80 ppm, and in the feed for fish or crustacea the carotenoid ester content is preferably from about 2.5 ppm to about 150 ppm.

The feed according to the present invention may contain in addition to the carotenoid ester of formula I conventional ingredients. The feed may be produced by conventional methods involving physical admixture, e.g., pelleting, extrusion, microencapsulation, and spraying, At some stage during the feed production process a carotenoid ester of formula I is incorporated. The conventional ingredients of poultry feed include, for example, wheat, maize, barley, sorghum, oats, rice, and soybean meal, usually in ground or broken form, as appropriate, in major proportions (at least about 10 percent by weight in each case). Further ingredients, in minor amounts (up to about 5 percent by weight, or in certain cases less than 1 percent by weight), include, for example, fish, meat, and bone meals, wheat bran, straw, yeast, hydrolysed fat, tallow, lard, limestone, salt, methionine premix, mineral premix, vitamin premix, and anticaking agent. Any poultry feed may be enriched with the carotenoid ester represented by formula I to produce a feed according to the present invention. Typically fish or crustacea feeds in accordance with the present invention include, aside from the added carotenoid ester, fish meal (as the major source of protein), wheat, bone meal, soybean meal, wheat flour, boiled starch, yeast, fish oil, soybean oil, soya lecithin, methionin, vitamins, and minerals. The protein, lipids, and carbohydrate content of such a feed is about 40–50%, about 15–40%, and about 10% by weight, respectively.

The carotenoid ester, and optionally, any further carotenoids for incorporation in the poultry, fish, or crustacea feed may be mixed in the form of beadlets (see EP 630,578 B1 and EP 718,284 B1 for typical beadlet compositions) into a so-called premix (see W. Steinberg, M. A. Grashorn, A.-M. Klünter, J. Schierle, "Comparative pigmentation efficiency of two products containing either apo-ester or tagetes extracts in egg yolks and liquid eggs," Arch. Geflügelk. 64 (4), 180–187 (2000)), which is added to the feed. The beadlets, which represent a further aspect of the present invention, may contain, aside from the carotenoid ester, a starch-coated matrix of gelatin and carbohydrate, and one or more anti-oxidants, e.g., ethoxyquin and ascorbyl palmitate.

The beadlets contain from about 1 to about 20 percent by weight of a carotenoid ester of formula I based on the total weight of the beadlet. Preferably the active ingredient in the beadlets is one or more of the carotenoid esters listed above ((1)–(19)), more preferably the cartenoid esters labelled (17)–(19). Preferebly, the premix contains from about 0.001 to about 15% by weight of the active ingredient based on the total weight of the premix.

The following examples are provided to further illustrate the compositions and methods of the present invention. These examples are illustrative only and are not intended to limit the scope of the invention in any way.

EXAMPLES

Example 1

Under an atmosphere of argon 5.26 g of (3-isopropoxycarbonyl-2-butenyl)-triphenylphosphonium chloride, 4 g of beta-apo-12'-carotenal, and 80 ml of methanol were mixed in a 200 ml flask (inert conditions). Thereafter, 2.23 ml of a 30% solution of sodium methylate in methanol was added dropwise to the mixture at 25° C. under inert conditions within 30 minutes with stirring. The reaction mixture was then stirred for 4 hours at 50° C. 82 ml of water and 0.34 ml of acetic acid were then added. Thereafter, the mixture was stirred at reflux temperature for 16 hours. The mixture was cooled to 0° C., and the resulting crystalline precipitate was collected by filtration and washed with two 12 ml portions of isopropanol and with 40 ml of water.

The product, crude isopropyl beta-apo-8'-carotenoate (about 9 g), was recrystallized from 140 ml of acetone with 7 ml of water, resulting in 3.6 g of red-brown crystals. The yield of isopropyl beta-apo-8'-carotenoate was 76% (total content of carotenoid ester approximately 97% according to HPLC).

This example illustrates the production of a compound of the invention (compound (17)) by the Wittig reaction.

Example 2

Under an atmosphere of argon 30.56 g of ethyl beta-apo-8'-carotenoate and 144.5 ml of 2-pentanol were dissolved in 250 ml of methylene chloride in a 750 ml flask, and 4.79 ml of a 30% solution of sodium methylate in methanol were added (inert conditions). The reaction mixture was heated and stirred at reflux temperature. The resulting ethanol was distilled off as an azeotropic mixture with methylene chloride. The distillate was substituted by fresh methylene chloride. The reaction was nearly complete after 3 hours, and after neutralization with 1.64 ml of acetic acid, the methylene chloride was substituted by methanol by means of distillation up to a vapor temperature of 65° C. The crystal suspension obtained was filtered, and the collected deep red crystalline precipitate was washed with methanol and water. After drying, 30.26 g of crude 2-pentyl beta-apo-8'-carotenoate were obtained in a yield of 90.7% (total content of carotenoid ester approximately 97% according to HPLC).

This example illustrates the production of a compound of the invention (compound (19)) by the transesterification method.

Example 3

Under an atmosphere of argon, 47.01 g of ethyl beta-apo-8'-carotenoate, 282 ml of tetrahydrofuran, 179 ml of ethanol, 41.26 g of potassium hydroxide, and 534 ml water were mixed in a reaction flask (inert conditions). The mixture was heated under reflux and stirred for 3 hours, during which all the solid components went into solution.

After cooling to 25° C. and adding 434.5 ml of hydrochloric acid (10% in water) the resulting suspension was filtered off under reduced pressure. The collected crystalline precipitate was then washed with 300 ml of water and dried at 60° C. under reduced pressure. 46.91 g of beta-apo-8'-carotenoic acid were obtained as violet-red crystals.

The crude beta-apo-8'-carotenoic acid, 440 ml of toluene, and 55.6 ml of trifluoroacetic acid anhydride were mixed and heated to 60° C. under an argon atmosphere to obtain a clear solution. 188 ml of tert. butanol were added dropwise within 10 minutes, and the solution was thereafter carefully neutralized with 120 g of 10% caustic soda. After the separation of the aqueous phase, the organic phase was washed with three 150 ml portions of water, and concentrated to dryness under reduced pressure. The oily residue was dissolved in 50 ml of acetone, and 200 ml of methanol was added with stirring under an argon atmosphere. The resulting crystal suspension was heated under reflux for 2 hours. After cooling at 25° C., filtration, washing with 150 ml of methanol, and drying under reduced pressure, 36.7 g of crude tert. butyl beta-apo-8'-carotenoate were obtained in a yield of 73.6% (total content of carotenoid ester approximately 82.9% according to HPLC).

This example illustrates the production of a compound of the invention (compound (18)) by the mixed anhydride method.

Example 4

Carotenoid Ester-Containing Beadlet Composition

| Constituent | Percent by weight |
| --- | --- |
| Carotenoid ester | 11.5% |
| Ethoxyquin | 2.2% |
| Ascorbyl palmitate | 1.1% |
| Gelatine, Bloom 140 | 31.0% |
| Dextrin Yellow | 13.2% |
| Sucrose (crystalline) | 13.2% |
| Corn starch | 27.8% |

Example 5

General

Pigmentation efficacy was assessed in egg yolk, in the back skin of the broiler carcass, and in broiler shanks by reflectance colorimetry accompanied by visual scoring (Roche Colour Fan). The deposition of the ethyl-β-apo-8'-carotenoate (control) and the other carotenoid esters was determined in egg yolk and in the broiler back skin. In addition, the carotenoid levels in plasma and abdominal fat were measured.

Materials and Methods for the Animal Trials in "Laying Hens"

The trials were carried out following the standard experimental design used for egg yolk pigmentation trials at the Roche Research Center for Animal Nutrition (CRNA, F-68305 Village-Neuf, France). Each year in February the pigmentation trials are started with a new flock of layers. At the beginning of the trials the age of the laying hens (192 birds, type 'ISA Brown') were as follows:

| H-19/98 | 51 weeks |
| --- | --- |
| H-25/98 | 59 weeks |
| H-12/99 | 36 weeks |
| H-18/99 | 60 weeks |
| H-05/00 | 23 weeks |

Preceding the trials the hens were fed a low carotenoid basal diet (produced at the CRNA) without carotenoid supplementation for at least 28 days. Details on the composition of the basal diet are listed in Table 1. During the trials, the control group received the low carotenoid basal diet containing less than 2 mg total xanthophylls per kg of feed. The other animals were fed this diet supplemented with the appropriate pigments for three weeks. The diet was given to the animals ad libitum in mash form. The hens had free access to tap water. Beside the unsupplemented control treatment, treatments were carried out involving the provision of supplemented feed, the results of these treatments being presented in Tables 7–9.

Materials and Methods for the Animal Trials in "Broilers"

The trials were carried out using chickens of the type Ross 308 (trials MC-24/98 and MC-02/99) and Ross 508 (trials MC-11/99, MC-16/99, MC-24/99, and MC-03/00) (Couvir de la Bohardière, F-49290 Saint Laurent de la Plaine). One-day old broiler chickens, separated by sex, were divided by weight into experimental groups of ten animals each and reared in floor pens littered with wood shavings. The chickens were fed a low carotenoid basal grower diet until day 22 (trials MC-24/98, MC-02/99, and MC-11/99) or until day 15 (trials MC-16/99, MC-24/99, and MC-03/00). The low carotenoid basal grower diet contained less than 2 mg total xanthophylls per kg of feed, and its composition is described in Table 2. For the subsequent experimental period of three weeks, the birds received the basal diet supplemented with an appropriate pigment. The feed was given in the form of crumbled pellets during the first week and as pellets thereafter. The animals had unrestricted access to feed and water. A given treatment involved one group of male and one group of female chickens. Each group of chickens was weighed at day 22 (trials MC-24/98, MC-02/99, and MC-11/99) or day 15 (trials MC-16/99, MC-24/99, and MC-03/00) and on day 43. On day 42, five chickens per group were selected at random, labelled, and blood samples were taken from the jugular vein. At the end of the experiment (day 44) the animals were slaughtered in a commercial slaughterhouse (Freyburger, Dannemarie, France). The following day, the color of the skin (hind back of carcasses) and the shanks of the labelled chicken were measured by reflectance colorimetry (Minolta CR 200 apparatus, CIE-Lab system). Samples of the dorsal skin and abdominal fat were obtained, pooled for each experimental group, and the carotenoid concentration was determined. The concentration of carotenoids in feed, plasma, skin, and abdominal fat was determined by standard procedures as described after Tables 1 and 2.

TABLE 1

Composition of basal feed for laying hens

| Ingredients | % Content |
| --- | --- |
| Wheat | 40.0 |
| Rice | 21.8 |
| Oats | 7.5 |

TABLE 1-continued

Composition of basal feed for laying hens

| Soybean meal (50% CP) | 14.0 | |
| --- | --- | --- |
| Soybean oil | 2.5 | |
| Fish meal (70% CP) | 4.0 | |
| Limestone | 7.8 | |
| Dicalcium phosphate | 1.3 | |
| Salt | 0.1 | |
| Vitamin/Mineral/Methionin-premix (1530, Agro Base) | 1.0 | |
| Calculated content (per kg) | | |
| Metabolizable energy | 11.8 | MJ |
| Crude protein | 177 | g |
| Crude fat | 46.6 | g |
| Lysine | 9.0 | g |
| Methionine + cysteine | 7.0 | g |
| Calcium | 37.2 | g |
| Available phosphorus | 3.9 | g |
| Vitamins (per kg) | | |

Vitamin A: 10'000 I.U.; vitamin $D_3$: 2'000 I.U.;
vitamin E: 10.0 mg; vitamin $K_3$: 1.02 mg;
vitamin $B_1$: 1.00 mg; vitamin $B_2$:
4.00 mg; vitamin $B_6$: 1.00 mg; vitamin $B_{12}$: 0.01 mg;
niacine: 20.0 mg; panthothenic acid: 6.0 mg; folic acid:
0.56 mg; biotin 0.05 mg; cholin: 30.0 mg
Minerals (per kg)

Na: 1.96 g; K: 5.18 g; Mg: 0.98 g; Mn: 124 mg;
Fe: 783 mg; Cu: 17.8 mg; Zn: 88.1 mg; I: 1.24
mg; Co: 1.05 mg; Se: 0.30 mg

TABLE 2

Composition of basal feed for broilers

| Ingredients | % Content |
| --- | --- |
| Wheat | 29.0 |
| Rice, broken | 28.0 |
| Soybean meal | 30.0 |
| Fish meal (70% CP) | 5.0 |
| Fat hydrolysed | 4.9 |
| Limestone | 0.6 |
| Salt | 0.2 |
| DL methionine | 0.2 |
| Dicalcium phosphate | 1.2 |
| Cholin chloride (75%) | 0.1 |
| Vitamin/Mineral-premix | 0.8 |
| Calculated content (per kg) | |
| Metabolizable energy | 12.97 MJ |
| Crude protein | 220.1 g |
| Crude fat | 65.4 g |
| Lysine | 12.8 g |
| Methionine + cysteine | 9.3 g |
| Calcium | 9.1 g |
| Available phosphorus | 4.49 g |
| Vitamins (per kg) | |

Vitamin A: 12'000 I.U.; vitamin $D_3$: 2'600 I.U.; vitamin C: 150 mg;
vitamin E: 64.4 mg; vitamin $K_3$: 3.1 mg; vitamin $B_1$: 3.0 mg;
vitamin $B_2$: 9.1 mg; vitamin $B_6$: 6.0 mg; vitamin $B_{12}$:
0.03 mg; niacine: 78.0 mg; panthothenic acid: 36.0 mg; folic acid: 1.5 mg;
biotin 0.08 mg; cholin: 1999 mg
Minerals (per kg)

Na: 1.52 g; Ca: 9.12 g; K: 8.21 g; Mg:
1.70 g; Fe: 197.7 mg; Cu: 20.2 mg; Zn:
62.1 mg; I: 0.94 mg; Co: 0.13 mg; Se:
0.30 mg

Methods of Measuring the Pigmentation Efficacy

Egg yolk color was assessed as described by Steinberg, et al. (Arch. Geflügelk 64 (4), 180–187 (2000)). The yolks were manually separated from the whites of the eggs. The isolated yolks of three to six eggs were combined, weighed, and stirred with a glass rod until the color appeared homogeneous. The color hue was visually scored using the Roche Yolk Colour Fan (RYCF, version 1993). An aliquot of the pooled egg yolks was transferred into a glass cuvette yielding an approximately 2 cm thick layer. The color was then measured by means of a Dr. Lange Xeno Color LS 100 spectro-colorimeter with diffuse D65-illumination and a 8° viewing angle.

The color of broiler skin and shanks was measured using a tristimulus Minolta CR-300 Chromameter with diffuse D65-illumination and a 0° viewing angle. The color of the skin was read at three different points on the back of the dry broiler carcasses and average values of the triple measurements were recorded. The color of shanks was measured using single measurements at the ball between the toes.

The color data were expressed as CIE $L^*a^*b^*$-values including $h^*$(hue) and $C^*$ (chroma). The values given in the tables per treatment and trial represent averages of color measurements of four egg yolk pools, ten broiler back skins, or ten broiler shanks (5 males and 5 females).

HPLC Analysis

The content of the various carotenoid esters in feed was determined according to the method of Schierle, et al. (J. Schierle, N. Faccin, V. Riegert, Analytical Methods for Vitamins and Carotenoids in Feed, Revised supplement: Determination of Stabilized Apocarotenoic Ester and Canthaxanthin in Premixes and Feeds, Roche publication no. 50771 (1995), publicly available from. F. Hoffmann-La Roche Ltd., CH-4070 Basel). This method was modified in that the mobile phase of the normal-phase HPLC contained 0.5% instead of 7% acetone in n-hexane, improving the separation of the E/Z-isomers of the carotenoid esters. Peaks were related to all-E- and Z-isomers of the various carotenoid esters by chromatography of heat-isomerized solutions of the respective reference substances in n-hexane. The HPLC system was calibrated with the all-E-isomer of ethyl β-apo-8'-carotenoate. The response factor of the various derivatives was deduced from that of ethyl β-apo-8'-carotenoate taking into account the respective molecular weight. The content of the Z-isomer fractions was calculated based on the response of the all-E-isomer and using a correction factor of 1.4 to account for the lower specific absorbance of the Z-isomers.

The HPLC-system for in-feed analysis was also used to quantify the carotenoid esters in egg yolk, broiler tissues, and broiler plasma, but the extraction procedure was different for the various matrices.

For plasma extraction, 1.0 g of the well-mixed plasma sample was introduced into a 10 ml test tube with 1.0 ml of demineralized water and 4.0 ml of ethanol, and the contents mixed on a Vortex shaker. After the addition of 4.0 ml n-hexane the test tube was sealed with a glass stopper and shaken for 5 minutes on a horizontal shaking device. The mixture was centrifuged for 5 minutes at about 2500 g to enhance the separation of the phases. An aliquot of the upper organic phase was injected by autosampler into the HPLC.

For the extraction of egg yolk, 10 g of pooled and homogenised yolk were mixed with 10 ml of demineralized water using a dispersion instrument (Polytron). 1.0 g of diluted egg yolk was introduced into a 10 ml test tube with 1.0 ml of demineralized water and 2.0 ml of ethanol, and the contents were mixed on a Vortex shaker. After addition of 4.0 ml of n-hexane, the mixture was further treated as described for plasma. Yolk lipid resulted in an expansion of the n-hexane phase from 4.0 to 4.3 ml, which was factored into the calculation of the carotenoid ester content.

Broiler back skin or abdominal fat from five male or female carcasses was pooled and homogenised using a Retsch Grindomix GM200. 1.0 g of the tissue paste was mixed with 1.0 g of magnesium sulphate hydrate and exhaustively extracted with three 8.0 ml portions of acetone by means of a dispersion instrument (Polytron). The combined extracts were filtered and evaporated under a flow of nitrogen at 50° C. The oily residue was dissolved and overall volume brought up to 10 ml in a volumetric flask with n-hexane containing 0.5% acetone. The solution was shaken and injected into the HPLC apparatus.

Pigments in Plasma, Skin, and Fat of Broilers

The concentration of isopropyl β-apo-8'-carotenoate (compound (17)) as equivalent of ethyl β-apo-8'-carotenoate in comparison with the controls (the commercial product CAROPHYLL® Yellow (ethyl β-apo-8'-carotenoate), so-called apo-ester), were 129% in plasma, 134% in skin, and 88% in fat. The comparable values for tert. butyl β-apo-8'-8'-carotenoate, (compound (18)) were 103%, 198%, and 113%, and 2-pentyl β-apo-8'-carotenoate (compound (19)) 88%, 134%, and 85%, respectively (Table 3). In comparison to the other 12 tested carotenoid esters (Table 4) the concentrations of compounds (17), (18), and (19) were determined as equivalents of the ethyl β-apo-8'-carotenoate and were, at least in the skin, substantially higher.

Reflectance Colorimetry

The increased values of pigment concentration in the skin were confirmed by the values of reflectance colorimetry in the skin and in the shanks. The chroma C*a*b* values were substantially enhanced, which indicated a more intensive color with compounds (17), (18), and (19) than with the control. The color hue h*a*b* was not significantly changed (Table 5). The increase in the determined chroma values was corroborated with the visual classification of the skin and shanks of the slaughtered broilers (Table 5). The color values of the other 12 tested carotenoid esters (Table 6) were in the range of the controls.

Three of the tested carotenoid esters (compounds (17), (18), and (19)) are significantly more effective in terms of concentration in the skin, and color intensity (chroma C*a*b*) in the skin and shanks than the control. The other 12 tested carotenoid esters have a quality comparable to the control.

Pigments in Egg Yolk

The analytical contents of the tested carotenoid esters as equivalent of ethyl β-apo-8'-carotenoate in comparison with the controls, the deposition rate, and the Roche Colour Fan Value (RYCF) are reported in Tables 7 and 8. The concentration in the egg yolk of compounds (17), (18), and (19) were in the range of the control (Table 7). The deposition rates (calculation of the deposition rate: Steinberg et al., Arch. Geflügelk. 64 (4), 180–187 (2000)) corresponded to the controls with a few exceptions (Tables 7 and 8).

Reflectance Colorimetry

The values of the carotenoid esters (color hue h*a*b* and chroma C*a*b*) and of the RYCF generally corresponded to the control values (Tables 9 and 10).

Compounds (17), (18), and (19) and the other 12 tested carotenoid esters have comparable quality compared to the control in terms of deposition rate and color intensity (chroma C*a*b*) in the egg yolk.

TABLE 3

Carotenoid content as equivalent of ethyl β-apo-8'-carotenoate in plasma, skin, and fat in relation to the controls of the same trial (Trials: MC-24/98, MC-02/99, MC-11/99, and MC-24/99)

| | | Doses | Analytical Content as Equivalent of Ethyl β-apo-8'-carotenoate | | | | | |
| | | mg/kg | Plasma | | Skin | | Fat | |
| Trial | Yellow Carotenoid | Feed | mg/kg | % | mg/kg | % | mg/kg | % |
| --- | --- | --- | --- | --- | --- | --- | --- | --- |
| MC-11/99 | Isopropyl β-apo-8'-carotenoate [17] | 8.88 | 6.0 | | 1.6 | | 1.2 | |
| MC-02/99 | Isopropyl β-apo-8'-carotenoate | 10 | 6.3 | | 2.0 | | 1.8 | |
| MC-11/99 | Isopropyl β-apo-8'-carotenoate | 13.33 | 8.6 | | 2.6 | | 1.9 | |
| MC-24/98 | Isopropyl β-apo-8'-carotenoate | 15 | 10.0 | | 2.5 | | 2.3 | |
| MC-02/99 | Isopropyl β-apo-8'-carotenoate | 20 | 13.4 | | 4.1 | | 3.3 | |
| MC-11/99 | Isopropyl β-apo-8'-carotenoate | 20 | 13.3 | | 3.7 | | 2.9 | |
| MC-24/98 | Isopropyl β-apo-8'-carotenoate | 30 | 19.9 | | 5.6 | | 4.5 | |
| MC-11/99 | Isopropyl β-apo-8'-carotenoate | 30 | 18.3 | | 6.1 | | 3.4 | |
| MC-11/99 | Isopropyl β-apo-8'-carotenoate | 45 | 30.6 | | 9.0 | | 6.4 | |
| | average | | | 129 | | 134 | | 88 |
| MC-24/99 | tert. Butyl β-apo-8'-carotenoate [18] | 20 | 12.2 | 117 | 5.4 | 194 | 3.7 | 119 |
| MC-24/99 | tert. Butyl β-apo-8'-carotenoate | 30 | 14.1 | 88 | 6.4 | 184 | 4.6 | 107 |
| | average | | | 103 | | 189 | | 113 |
| MC-24/99 | 2-Pentyl β-apo-8'-carotenoate [19] | 20 | 9.6 | 93 | 3.6 | 128 | 2.6 | 83 |
| MC-24/99 | 2-Pentyl β-apo-8'-carotenoate | 30 | 13.3 | 82 | 4.8 | 139 | 3.8 | 87 |
| | average | | | 88 | | 134 | | 85 |

TABLE 4

Carotenoid content as equivalent of ethyl β-apo-8'-carotenoate in plasma, skin, and fat in relation to the controls (Trials: MC-11/99, MC-16/99, MC-24/99, and MC-03/00)

| | | | Analytical Content as Equivalent of Ethyl β-apo-8'-carotenoate in % of control | | |
| | | Doses | | | |
| Trial | Yellow Carotenoid | mg/kg Feed | Plasma % | Skin % | Fat % |
| --- | --- | --- | --- | --- | --- |
| MC-16/99 | Methyl β-apo-8'-carotenoate [1] | average | 88 | 87 | 85 |
| MC-11/99 | n-Propyl β-apo-8'-carotenoate [2] | average | 68 | 45 | 39 |
| MC-16/99 | Isobutyl β-apo-8'-carotenoate [4] | average | 58 | not detectable | not detectable |

TABLE 4-continued

Carotenoid content as equivalent of ethyl β-apo-8'-carotenoate in plasma, skin, and fat in relation to the controls (Trials: MC-11/99, MC-16/99, MC-24/99, and MC-03/00)

| Trial | Yellow Carotenoid | Doses mg/kg Feed | Analytical Content as Equivalent of Ethyl β-apo-8'-carotenoate in % of control | | |
|---|---|---|---|---|---|
| | | | Plasma % | Skin % | Fat % |
| MC-16/99 | sec. Butyl β-apo-8'-carotenoate [5] | average | 94 | 74 | 53 |
| MC-03/00 | Cyclopentyl β-apo-8'-carotenoate [15] | average | 76 | 77 | 50 |
| MC-16/99 | Isoamyl β-apo-8'-carotenoate [6] | average | 62 | 38 | 35 |
| MC-24/99 | 2-Methyl-butyl β-apo-8'-carotenoate [7] | average | 62 | 40 | 45 |
| MC-24/99 | 2,2-Dimethyl-propyl β-apo-8'-carotenoate [8] | average | 78 | 76 | 62 |
| MC-24/99 | Cyclohexyl β-apo-8'-carotenoate [16] | average | 60 | 44 | 38 |
| MC-24/99 | 2-Methyl-1-pentyl β-apo-8'-carotenoate [11] | average | 59 | 69 | 50 |
| MC-24/99 | 2-Ethyl-1-butyl β-apo-8'-carotenoate [9] | average | 59 | 55 | 45 |
| MC-24/99 | 4-Methyl-2-pentyl β-apo-8'-carotenoate [12] | average | 66 | 85 | 49 |

TABLE 5

Yellow carotenoids; values of reflectance colorimetry (CIE-Lab system, Minolta Chromameter) for skin and shanks of broilers, dry carcasses (Trials: MC-24/98, MC-11/99, and MC-24/99)

| Trial | Yellow Carotenoid | Doses mg/kg Feed | Skin | | | | | Shanks | | | | |
|---|---|---|---|---|---|---|---|---|---|---|---|---|
| | | | Color Hue h*ab | | Chroma C*ab | | Visual | Color Hue h*ab | | Chroma C*ab | | Visual |
| | | | Value | % of Controls | Value | % of Controls | Classification | Value | % of Controls | Value | % of Controls | Classification |
| MC-11/99 | Isopropyl β-apo-8'-carotenoate | 13.33 | 77 | 105 | 29 | 116 | (+) | 84 | 99 | 70 | 97 | (+) |
| MC-11/99 | Isopropyl β-apo-8'-carotenoate | 20 | 78 | 100 | 33 | 106 | + | 87 | 103 | 59 | 125 | + |
| MC-24/98 | Isopropyl β-apo-8'-carotenoate | 30 | 82 | 102 | 39 | 119 | + | 80 | 93 | 71 | 137 | + |
| MC-11/99 | Isopropyl β-apo-8'-carotenoate | 30 | 79 | 102 | 40 | 119 | + | 83 | 97 | 65 | 108 | + |
| MC-11/99 | Isopropyl β-apo-8'-carotenoate | 45 | 79 | 103 | 44 | 105 | ++ | 84 | 101 | 71 | 108 | ++(o) |
| | average | | | 102 | | 113 | | | 99 | | 115 | |
| MC-24/99 | tert. Butyl β-apo-8'-carotenoate | 20 | 81 | 107 | 38 | 116 | + | 84 | 100 | 63 | 114 | + |
| MC-24/99 | tert. Butyl β-apo-8'-carotenoate | 30 | 80 | 102 | 41 | 113 | ++ | 82 | 99 | 70 | 111 | ++ |
| | average | | | 105 | | 115 | | | 100 | | 113 | |
| MC-24/99 | 2-Pentyl β-apo-8'-carotenoate [19] | 20 | 73 | 96 | 34 | 106 | + | 82 | 98 | 60 | 108 | + |
| MC-24/99 | 2-Pentyl β-apo-8'-carotenoate | 30 | 76 | 97 | 38 | 105 | +(+) | 82 | 98 | 65 | 102 | ++ |
| | average | | | 97 | | 106 | | | 98 | | 105 | |

Pigmentation: −; (+); +; ++ = good color; o = orange

TABLE 6

Yellow carotenoids; % values of reflectance colorimetry (CIE-Lab system, Minolta Chromameter) for skin and shanks of broilers, dry carcasses (Trials: MC-11/99, MC-16/99, MC-24/99, and MC-03/00)

| Trial | Yellow Carotenoid | Doses mg/kg Feed | Skin | | | Shanks | | |
|---|---|---|---|---|---|---|---|---|
| | | | Color Hue h*ab % of Controls | Chroma C*ab % of Controls | Visual Classification | Color Hue h*ab % of Controls | Chroma C*ab % of Controls | Visual Classification |
| MC-16/99 | Methyl β-apo-8'-carotenoate [1] | average | 100 | 97 | (+) | 101 | 97 | (+) |
| MC-11/99 | n-Propyl β-apo-8'-carotenoate [2] | average | 97 | 93 | (+) | 99 | 108 | (+) |
| MC-16/99 | Isobutyl β-apo-8'-carotenoate [4] | average | 98 | 84 | (+) | 105 | 72 | (+) |
| MC-16/99 | sec. Butyl β-apo-8'-carotenoate [5] | average | 101 | 100 | + | 101 | 100 | + |
| MC-03/00 | Cyclopentyl β-apo-8'-carotenoate [15] | average | 99 | 106 | ++ | 100 | 99 | ++ |
| MC-16/99 | Isoamyl β-apo-8'-carotenoate [6] | average | 99 | 89 | (+) | 101 | 86 | (+) |
| MC-24/99 | 2-Methyl-butyl β-apo-8'-carotenoate [7] | average | 94 | 80 | (+) | 101 | 85 | (+) |
| MC-24/99 | 2,2-Dimethyl-propyl β-apo-8'-carotenoate [8] | average | 100 | 98 | (+) | 101 | 98 | (+) |
| MC-24/99 | Cyclohexyl β-apo-8'-carotenoate [16] | average | 95 | 80 | + | 103 | 84 | (+) |

TABLE 6-continued

Yellow carotenoids; % values of reflectance colorimetry (CIE-Lab system, Minolta Chromameter) for skin and shanks of broilers, dry carcasses (Trials: MC-11/99, MC-16/99, MC-24/99, and MC-03/00)

| | | | Skin | | | Shanks | | |
|---|---|---|---|---|---|---|---|---|
| Trial | Yellow Carotenoid | Doses mg/kg Feed | Color Hue h*ab % of Controls | Chroma C*ab % of Controls | Visual Classification | Color Hue h*ab % of Controls | Chroma C*ab % of Controls | Visual Classification |
| MC-24/99 | 2-Methyl-l-pentyl β-apo-8'-carotenoate [11] | average | 95 | 87 | + | 101 | 92 | (+) |
| MC-24/99 | 2-Ethyl-l-butyl β-apo-8'-carotenoate [9] | average | 101 | 82 | + | 101 | 92 | (+) |
| MC-24/99 | 4-Methyl-2-pentyl β-apo-8'-carotenoate [12] | average | 99 | 91 | + | 101 | 95 | + |

Pigmentation: −; (+); +; ++ = good color; o = orange

TABLE 7

Carotenoid content as equivalent of ethyl β-apo-8'-carotenoate, deposition rate, and color fan value of yellow carotenoids in egg yolk in relation to the controls of the same trials (Trials: H-19/98, H-25/98, H-12/99, and H-25/99)

| | | | Ethyl β-apo-8'-carotenoate Equivalents | | Deposition Rate Target Values | | Color Fan Value | |
|---|---|---|---|---|---|---|---|---|
| Trial | Yellow Carotenoid | Doses mg/kg Feed | mg/kg | % of Controls | % | % of Controls | Value*) | % of Controls |
| H-12/99 | Isopropyl β-apo-8'-carotenoate [17] | 1.0 | 2.6 | 97 | 44 | 97 | 3 (+) | 66 |
| H-12/99 | Isopropyl β-apo-8'-carotenoate | 2.0 | 5.2 | 94 | 44 | 100 | 6 + | 104 |
| H-19/98 | Isopropyl β-apo-8'-carotenoate | 4.0 | 11.1 | 95 | 54 | 117 | 5 + | 79 |
| H-12/99 | Isopropyl β-apo-8'-carotenoate | 4.0 | 9.6 | 81 | 42 | 85 | 6 + | 97 |
| H-25/99 | Isopropyl β-apo-8'-carotenoate | 5.0 | 13.3 | 84 | 50 | 100 | 9 ++ | 130 |
| H-12/99 | Isopropyl β-apo-8'-carotenoate | 8.0 | 23.1 | 96 | 49 | 104 | 9 + | 156 |
| | average | | | 91 | | 101 | | 105 |
| H-25/99 | tert. Butyl β-apo-8'-carotenoate [18] | 5.0 | 16.6 | 106 | 60.7 | 119 | 7 + | 87 |
| | average | | | 106 | | 119 | | 87 |
| H-25/99 | 2-Pentyl β-apo-8'-carotenoate | 5.0 | 14.6 | 94 | 51.2 | 101 | 7 + | 87 |
| | average | | | 94 | | 101 | | 87 |

*)Pigmentation: − = off color; + = good color

TABLE 8

Carotenoid content as equivalent of ethyl β-apo-8'-carotenoate, deposition rate, and color fan value of yellow carotenoids in egg yolk in relation to the controls (Trials: H-19/98, H-25/98, H-12/99, H-18/99, H-22/99, H-25/99, and H-05/00

| Trial | Yellow Carotenoid | Doses mg/kg Feed | Ethyl β-apo-8'-carotenoate Equivalents % of Controls | Deposition Rate Target Values % of Controls | Color Fan Value % of Controls |
|---|---|---|---|---|---|
| n = 16 | Control: Ethyl β-apo-8'-carotenoate | 1.0–8.0 | 100 | 100 | 100 |
| H-18/99 | Methyl β-apo-8'-carotenoate [1] | 5.0 | 95 | 99 | 130 |
| H-12/99 | n-Propyl β-apo-8'-carotenoate [2] | 2; 4; 8 | 73 | 77 | 110 |
| H-18/99 | Isobutyl β-apo-8'-carotenoate [4] | 5.0 | 74 | 83 | 116 |
| H-18; 22/99 | sec. Butyl β-apo-8'-carotenoate [5] | 1; 2; 4; 5; 8 | 90 | 97 | 88 |
| H-05/00 | Cyclopentyl β-apo-8'-carotenoate [15] | 5.0 | 95 | 95 | 116 |
| H-18/99 | Isoamyl β-apo-8'-carotenoate [6] | 5.0 | 80 | 90 | 116 |
| H-25/99 | 2-Methyl-butyl β-apo-8'-carotenoate [7] | 5.0 | 86 | 95 | 108 |
| H-25/99 | 2,2-Dimethyl-propyl β-apo-8'-carotenoate [8] | 5.0 | 81 | 89 | 108 |
| H-25/99 | Cyclohexyl β-apo-8'-carotenoate [16] | 5.0 | 82 | 99 | 108 |
| H-25/99 | 2-Methyl-1-pentyl β-apo-8'-carotenoate [11] | 5.0 | 96 | 112 | 116 |

TABLE 8-continued

Carotenoid content as equivalent of ethyl β-apo-8'-carotenoate, deposition rate, and color fan value of yellow carotenoids in egg yolk in relation to the controls (Trials: H-19/98, H-25/98, H-12/99, H-18/99, H-22/99, H-25/99, and H-05/00)

| Trial | Yellow Carotenoid | Doses mg/kg Feed | Ethyl β-apo-8'-carotenoate Equivalents % of Controls | Deposition Rate Target Values % of Controls | Color Fan Value % of Controls |
|---|---|---|---|---|---|
| H-25/99 | 2-Ethyl-1-butyl β-apo-8'-carotenoate [9] | 5.0 | 77 | 87 | 101 |
| H-25/99 | 4-Methyl-2-pentyl β-apo-8'-carotenoate [12] | 5.0 | 79 | 89 | 101 |

TABLE 9

Values of reflectance colorimetry, deposition rate, and color fan value of yellow carotenoids in egg yolk in relation to the controls of the same trials (CIE-Lab system, Xenocolor Chromameter) (Trials: H-19/98, H-25/98, H-12/99, and H-25/99)

| Trial | Yellow Carotenoid | Doses mg/kg Feed | Color Hue h*ab Value | Color Hue h*ab % of Controls | Chroma C*ab Value | Chroma C*ab % of Controls | Deposition Rate Value | Deposition Rate % of Controls | Color Fan Value Value | Color Fan Value % of Controls |
|---|---|---|---|---|---|---|---|---|---|---|
| H-12/99 | Isopropyl β-apo-8'-carotenoate [17] | 1.0 | 95 | 101 | 39 | 98 | 44 | 97 | 3 (+) | 66 |
| H-12/99 | Isopropyl β-apo-8'-carotenoate | 2.0 | 93 | 101 | 45 | 100 | 44 | 100 | 6 + | 104 |
| H-19/98 | Isopropyl β-apo-8'-carotenoate | 4.0 | 89 | 106 | 51 | 97 | 54 | 117 | 5 + | 79 |
| H-12/99 | Isopropyl β-apo-8'-carotenoate | 4.0 | 90 | 102 | 51 | 98 | 42 | 85 | 6 + | 97 |
| H-25/98 | Isopropyl β-apo-8'-carotenoate | 5.0 | 86 | 98 | 52 | 99 | 50 | 106 | 9 ++ | 130 |
| H-12/99 | Isopropyl β-apo-8'-carotenoate | 8.0 | 85 | 100 | 54 | 96 | 49 | 104 | 9 + | 156 |
|  | average |  |  | 101 |  | 98 |  | 101 |  | 105 |
| H-25/99 | tert. Butyl β-apo-8'-carotenoate [18] | 5.0 | 74 | 85 | 52 | 101 | 61 | 119 | 7 + | 87 |
|  | average |  |  | 85 |  | 101 |  | 119 |  | 87 |
| H-25/99 | 2-Pentyl β-apo-8'-carotenoate [19] | 5.0 | 82 | 96 | 58 | 113 | 51 | 101 | 7 + | 87 |
|  | average |  |  | 96 |  | 113 |  | 101 |  | 87 |

*)Pigmentation – = off color; + = good color

TABLE 10

Values of reflectance colorimetry, deposition rate, and color fan value of yellow carotenoids in egg yolk in relation to the controls of the same trials (CIE-Lab system, Xenocolor Chromameter) (Trials: H-19/98, H-25/98, H-12/99, H-15/99, H-18/99, H-22/99, H-25/99, and H-05/00)

| Trial | Yellow Carotenoid | Doses mg/kg Feed | Color Hue h*ab % of Controls | Chroma C*ab % of Controls | Deposition Rate % of Controls | Color Fan Value % of Controls |
|---|---|---|---|---|---|---|
| H-18/99 | Methyl β-apo-8'-carotenoate [1] | 5.0 | 99 | 104 | 99 | 130 |
| H-12/99 | n-Propyl β-apo-8'-carotenoate [2] | 2; 4; 8 | 101 | 95 | 77 | 110 |
| H-18/99 | Isobutyl β-apo-8'-carotenoate [4] | 5.0 | 101 | 104 | 83 | 116 |
| H-18; 22/99 | sec. Butyl β-apo-8'-carotenoate [5] | 1; 2; 4; 5; 8 | 102 | 103 | 84[1)] | 93[1)] |
| H-05/00 | Cyclopentyl β-apo-8'-carotenoate [15] | 5.0 | 101 | 107 | 95 | 116 |
| H-18/99 | Isoamyl β-apo-8'-carotenoate [6] | 5.0 | 101 | 105 | 90 | 116 |
| H-25/99 | 2-Methyl-butyl β-apo-8'-carotenoate [7] | 5.0 | 106 | 87 | 95 | 108 |

TABLE 10-continued

Values of reflectance colorimetry, deposition rate, and color fan
value of yellow carotenoids in egg yolk in relation to the controls
of the same trials (CIE-Lab system, Xenocolor Chromameter)
(Trials: H-19/98, H-25/98, H-12/99, H-15/99, H-18/99, H-22/99,
H-25/99, and H-05/00

| Trial | Yellow Carotenoid | Doses mg/kg Feed | Color Hue h*ab % of Controls | Chroma C*ab % of Controls | Deposition Rate % of Controls | Color Fan Value % of Controls |
|---|---|---|---|---|---|---|
| H-25/99 | 2,2-Dimethyl-propyl β-apo-8'-carotenoate [8] | 5.0 | 101 | 94 | 89 | 108 |
| H-25/99 | Cyclohexyl β-apo-8'-carotenoate [16] | 5.0 | 97 | 112 | 99 | 108 |
| H-25/99 | 2-Methyl-1-pentyl β-apo-8'-carotenoate [11] | 5.0 | 103 | 101 | 112 | 116 |
| H-25/99 | 2-Ethyl-1-butyl β-apo-8'-carotenoate [9] | 5.0 | 92 | 99 | 87 | 101 |
| H-25/99 | 4-Methyl-2-pentyl β-apo-8'-carotenoate [12] | 5.0 | 109 | 74 | 89 | 101 |

[1])comparison within same trials

The invention being thus described, it will be obvious that the same may be varied in many ways. Such variations are not to be regarded as a departure from the spirit and scope of the invention and all such modifications are intended to be included within the scope of the following claims.

What is claimed is:

1. A method for pigmenting a food or food stuff comprising combining in a source of feed, a beadlet comprising from about 1 to about 20 percent by weight based on the total weight of the beadlet of a carotenoid ester selected from the group consisting of isopropyl-8'-cartoenoate, tert. butyl β-apo8'-carotenoate, 2-pentyl β-apo-8'-cartoenoate, and combinations thereof.

2. A method according to claim 1 wherein the amount of carotenoid ester in the feed is from about 0.1 ppm to about 150 ppm based on the total weight of the carotenoid ester-enriched feed.

3. A method according to claim 1 wherein the amount of carotenoid ester in the feed is from about 0.25 ppm to about 80 ppm, for laying hens and broilers.

4. A method according to claim 1 wherein the amount of carotenoid ester in the feed is from about 2.5 ppm to about 150 ppm, said feed being feed for fish or crustacea.

5. A method according to claim 1 wherein the food or feed stuff is selected from the group consisting of egg yolk, integuments or subcutaneous fat of poultry, and the meat or integuments of fish or crustacea.

6. A method according to claim 1 further comprising feeding the feed source to laying hens or broilers to produce a pigmented egg yolk.

7. A carotenoid-enriched feed comprising a beadlet comprising from about 1 to about 20 percent by weight based on the total weight of the beadlet a carotenoid ester selected from the group consisting of isopropyl-8'-carotenoate, tert. butyl β-apo-8'-carotenoate, 2-pentyl β-apo-8'-carotenoate, and combination thereof.

8. A carotenoid-enriched feed according to claim 7 wherein the amount of the carotenoid ester in the feed is from about 0.1 ppm to about 150 ppm based on the total weight of the carotenoid-enriched feed.

9. A carotenoid-enriched feed according to claim 7 wherein the feed is a feed for an organism selected from the group consisting of poultry, fish, and crustacea.

10. A carotenoid-enriched feed according to claim 9 wherein the feed is a feed for poultry.

11. A beadlet comprising from about 1 to about 20 percent by weight based on the total weight of the beadlet of a carotenoid ester selected from a group consisting of isopropyl-8'-carotenoate, tert. butyl β-apo-8'-carotenoate, 2-pentyl β-apo-8'-carotenoate, and combinations thereof.

12. A beadlet according to claim 11 further comprising at least one additional carotenoid.

13. A premix comprising a beadlet according to claim 11 wherein the amount of the carotenoid ester in the premix is from about 0.001 to about 15% by weight based on the total weight of the premix.

14. A premix according to claim 13 wherein the feed is a feed for an organism selected from the group consisting of poultry, fish, and crustacea.

15. A premix according to claim 13 wherein the beadlet comprises at least one additional carotenoid.

16. A method for pigmenting an organism comprising orally administering to the organism a carotenoid-enriched feed comprising a beadlet comprising from about 1 to about 20 percent by weight based on the total weight of the beadlet of a carotenoid ester selected from the group consisting of isopropyl-8'-carotenoate, tert. butyl β-apo-8'-carotenoate, 2-pentyl β-apo-8'-carotenoate, and combinations thereof.

17. A method according to claim 16 wherein the organism is selected from the group consisting of poultry, fish, and crustacea.

18. A method according to claim 17 wherein the quantity of the carotenoid ester orally administered to the poultry, fish, or crustacea is sufficient to pigment egg yolk produced by the poultry or the integuments or subcutaneous fat of poultry or the meat or integuments of fish or crustacea.

* * * * *

UNITED STATES PATENT AND TRADEMARK OFFICE
CERTIFICATE OF CORRECTION

PATENT NO. : 6,896,895 B2
DATED : May 24, 2005
INVENTOR(S) : Joseph Schierle, Werner Simon and Wolfgang Steinberg It is certified that error appears in the above-identified patent and that said Letters Patent is hereby corrected as shown below:

Column 19,
Line 38, please change "isopropyl-8'-carotenoate" to -- isopropyl $\beta$-apo-8'-carotenoate --.

Column 20,
Lines 9, 24 and 42, please change "isopropyl-8'-carotenoate" to -- isopropyl $\beta$-apo-8'-carotenoate --.

Signed and Sealed this

Sixth Day of September, 2005

JON W. DUDAS
*Director of the United States Patent and Trademark Office*